US012784381B2

(12) United States Patent
Qian et al.

(10) Patent No.: US 12,784,381 B2
(45) Date of Patent: Nov. 3, 2026

(54) ULTRASOUND SITUATED DISPLAY IN AN AUGMENTED REALITY ENVIRONMENT

(71) Applicant: Medivis, Inc., New York, NY (US)

(72) Inventors: Long Qian, Brooklyn, NY (US); Osamah Choudhry, New York, NY (US); Christopher Morley, New York, NY (US); Joseph Benjamin Horowitz, New York, NY (US)

(73) Assignee: Medivis, Inc., New York, NY (US)

( * ) Notice: Subject to any disclaimer, the term of this patent is extended or adjusted under 35 U.S.C. 154(b) by 103 days.

(21) Appl. No.: 18/748,328

(22) Filed: Jun. 20, 2024

(65) Prior Publication Data

US 2025/0391121 A1 Dec. 25, 2025

(51) Int. Cl.

| | |
|---|---|
| ***G06T 19/00*** | (2011.01) |
| ***A61B 8/00*** | (2006.01) |
| ***G06F 3/01*** | (2006.01) |
| ***G06T 19/20*** | (2011.01) |
| ***G09B 23/28*** | (2006.01) |

(52) U.S. Cl.

CPC ............ *G06T 19/006* (2013.01); *A61B 8/466* (2013.01); *A61B 8/587* (2013.01); *G06F 3/012* (2013.01); *G06T 19/20* (2013.01); *G09B 23/286* (2013.01); *G06T 2200/24* (2013.01); *G06T 2210/41* (2013.01); *G06T 2219/2004* (2013.01); *G06T 2219/2016* (2013.01)

(58) Field of Classification Search

None

See application file for complete search history.

(56) References Cited

U.S. PATENT DOCUMENTS

| | | | | |
|---|---|---|---|---|
| 2002/0156864 A1* | 10/2002 | Kniest | A61B 8/00 | 709/227 |
| 2010/0331699 A1* | 12/2010 | Yu | A61B 8/0825 | 600/446 |
| 2014/0078138 A1* | 3/2014 | Martin | A61B 8/0841 | 345/420 |
| 2017/0360412 A1* | 12/2017 | Rothberg | A61B 8/5207 | |
| 2019/0307518 A1* | 10/2019 | Schotzko | A61B 34/20 | |

* cited by examiner

*Primary Examiner* — Nicholas R Wilson

(74) *Attorney, Agent, or Firm* — Cognition IP, P.C.; Edward Steakley; Saleh Kaihani

(57) ABSTRACT

An example operation(s) includes defining a display position of an image plane proximate to a current position of an ultrasound probe instrument. An Augmented Reality (AR) situated view is rendered on the image plane, the situated view portrays ultrasound imagery captured by the ultrasound probe instrument. An AR display orientation of the image plane is determined based on one or more detected movements of the AR headset device. One or more portions of the ultrasound imagery are registered as being representative of respective portions of a three-dimensional (3D) medical model.

20 Claims, 14 Drawing Sheets

ULTRASOUND SITUATED DISPLAY IN AN AUGMENTED REALITY ENVIRONMENT

FIELD OF INVENTION

Various embodiments relate generally to augmented reality and more specifically to merging ultrasound data to provide an augmented reality (AR) model.

SUMMARY

The appended claims may serve as a summary of this application. Various embodiments described herein provide improvements to conventional ultrasound systems by rendering ultrasound imagery as an AR overlay near a current position of an ultrasound probe-instead of only displaying imagery on a physical display screen. By rendering the ultrasound imagery in an AR environment so that it appears as an overlay near physical anatomy visualized by the ultrasound probe, an individual manually controlling the ultrasound probe gains greater visual context and anatomical awareness of a cross-section of a patient's anatomy that is being portrayed via ultrasound imagery.

In various embodiments, the AR overlay may be a situated view of ultrasound imagery captured by an ultrasound probe ("probe"). The situated view is displayed proximate to a current position of the probe's tip. As the probe is inserted into the physical internal anatomy of a patient, the situated view may be displayed above a surface of the patient, but still relatively proximate to the position of the probe's tip while the probe is inside the patient. The ultrasound imagery portrayed by the situated view may be updated based on changes of a current position and physical orientation of the probe.

According to various embodiments, the situated view may be rendered according to an image plane having coordinates defined by a unified three-dimensional (3D) coordinate system. The image plane determines positioning of the situated view in an AR environment rendered by an AR headset. Where the ultrasound imagery of the situated view is modified in response to changes in the current position and physical orientation of the probe, the orientation of the situated view's image plane changes in response to detected changes in a current position and physical orientation of the headset. For example, the situated view may be displayed proximate to a position of the probe's tip and the physical orientation (i.e. angle) of the situated view's image plane may be titled to correspond with detected movement of the headset. That is, the situated view may be displayed in the AR environment as both proximate to the probe's tip and as gradually tilting based on detecting continuous movement of the headset. As the situated view is displayed in the AR environment as tilting due to the changes in the positioning of its image plane, the ultrasound imagery within the situated view is modified responsive to movement of the probe—but not responsive to the headset's detected movement. This enables the headset to move around and view a positional view of the ultrasound imagery without changing the areas where the ultrasound imagery is originating based on the probe.

Various embodiments include one or more calibrations that define a pixel of ultrasound imagery as corresponding to a particular distance. The calibration can be adjusted according to a virtual menu displayed in the AR environment. The virtual menu selection may be used to adjust a depth setting whereby changes in the calibration determine changes in how much distance is represented per pixel of ultrasound imagery.

According to various embodiments, a virtual sensor ("sensor") may be concurrently displayed with the situated view in the AR environment. The sensor may also be an overlay displayed proximate to a patient and have its position defined according to the unified three-dimensional (3D) coordinate system. As such, respective positions in 3D space of the sensor and probe can be continuously tracked and known. The sensor and probe thereby provide known reference positions with respect to the position and physical orientation of the patient, while the situated view displays ultrasound imagery visualized via the probe and the positioning of the situated view's image plane adjusts according to movement of the headset.

Various embodiments utilize the reference positions of the sensor and probe and the calibration (i.e. pixels per distance) level for performance of a liner transformation algorithm to determine a display position of the situated view's image plane that is proximate to the probe's tip. Various embodiments may include a 3D medical model of the patient's anatomy and may provide for registering portions of the 3D medical model with the ultrasound imagery portrayed in the situated view. The 3D medical model may be portrayed as a virtual object in the AR environment that can be moved and manipulated in response to physical gestures applied to the virtual object.

In some embodiments, the 3D medical model may represent internal anatomy that is being visualized in the situated view based on the probe position. The user may perform respective physical gestures thereby adjusting a display position of the 3D medical model in the AR environment that results in aligning the visualization of the internal anatomy offered by the 3D medical model with real-time ultrasound imagery of the same internal anatomy portrayed in the situated view. Once the 3D medical model appears to the user as being visually aligned in the AR environment with the depiction of the same internal anatomy shown in the situated view, the user may select to register the current position and physical orientation of the 3D medical model.

According to various embodiments, once the 3D medical model is registered, the position and physical orientation of the probe may still change in response to how it is being handled by the individual manually controlling the probe. The situated view may thereby be updated to portray changes in the ultrasound imagery that correspond to changes to the position and physical orientation of the probe while engaged with the anatomical structure of the patient. Since positions of the situated view and the registered 3D medical model are known according to the unified 3D coordinate system, collisions between portions of the situated view and portions of the registered 3D medical model may be detected as the probe is physically moved. Those portions of the ultrasound imagery in the situated view that collide with the registered 3D medical model may be obscured so as to prioritize display in the AR environment of the visualization of the internal anatomy provided by the registered 3D medical model.

BRIEF DESCRIPTION OF THE DRAWINGS

The present invention relates generally to AR visualization for identifying ultrasound areas of a medical patient by a medical professional.

The present disclosure will become better understood from the detailed description and the drawings, wherein.

DETAILED DESCRIPTION

It will be readily understood that the instant components, as generally described and illustrated in the figures herein, may be arranged and designed in a wide variety of different configurations. Thus, the following detailed description of the embodiments of at least one of a method, apparatus, computer readable storage medium and system, as represented in the attached figures, is not intended to limit the scope of the application as claimed but is merely representative of selected embodiments. Multiple embodiments depicted herein are not intended to limit the scope of the solution. The computer-readable storage medium may be a non-transitory computer readable media or a non-transitory computer readable storage medium.

The instant features, structures, or characteristics described in this specification may be combined in any suitable manner in one or more embodiments. For example, the usage of the phrases "example embodiments," "some embodiments," or other similar language, throughout this specification refers to the fact that a particular feature, structure, or characteristic described in connection with the embodiment may be included in at least one example. Thus, appearances of the phrases "example embodiments", "in some embodiments", "in other embodiments," or other similar language, throughout this specification can all refer to the same embodiment. Thus, these embodiments may work in conjunction with any of the other embodiments, may not be functionally separate, and the described features, structures, or characteristics may be combined in any suitable manner in one or more embodiments.

Example embodiments provide methods, systems, hardware components, non-transitory computer readable media, devices, and/or networks, which provide for visualizing tractography data to identify a region of interest (ROI) of a person/patient. The patient may be a candidate for a surgical procedure, such as brain surgery, open heart surgery, orthopedic surgery of a joint or bone, etc.

Figure 1A:
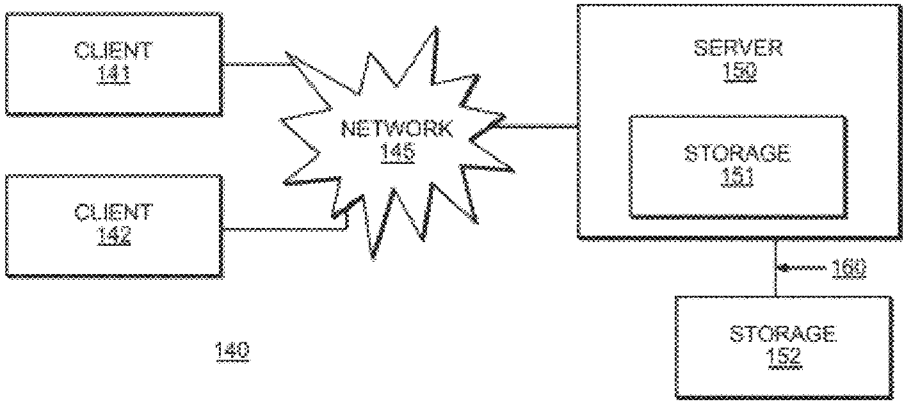
FIG. 1A illustrates an example network configuration according to example embodiments.

A diagram of an exemplary network environment in which embodiments may operate is shown in FIG. 1A. In the exemplary environment 140, two clients 141, 142 are connected over a network 145 to a server 150 having local storage 151. Clients and servers in this environment may be computers. Server 150 may be configured to handle requests from clients.

The exemplary environment 140 is illustrated with only two clients and one server for simplicity, though in practice there may be more or fewer clients and servers. The computers have been termed clients and servers, though clients can also play the role of servers and servers can also play the role of clients. In some embodiments, the clients 141, 142 may communicate with each other as well as the servers. Also, the server 150 may communicate with other servers.

The network 145 may be, for example, a local area network (LAN), a wide area network (WAN), telephone networks, wireless networks, intranets, the Internet, or combinations of networks. The server 150 may be connected to storage 152 over a connection medium 160, which may be a bus, crossbar, network, or other interconnect. Storage 152 may be implemented as a network of multiple storage devices, though it is illustrated as a single entity. Storage 152 may be a file system, disk, database, or other storage.

In an embodiment, the client 141 may perform the method 200 or other method herein and, as a result, store a file in the storage 152. This may be accomplished via communication over the network 145 between the client 141 and server 150. For example, the client may communicate a request to the server 150 to store a file with a specified name in the storage 152. The server 150 may respond to the request and store the file with the specified name in the storage 152. The file to be saved may exist on the client 141 or may already exist in the server's local storage 151. In another embodiment, the server 150 may respond to requests and store the file with a specified name in the storage 151. The file to be saved may exist on the client 141 or may exist in other storage accessible via the network such as storage 152, or even in storage on the client 142 (e.g., in a peer-to-peer system).

In accordance with the above discussion, embodiments can be used to store a file on local storage such as a disk or on a removable medium like a flash drive, CD-R, or DVD-R. Furthermore, embodiments may be used to store a file on an external storage device connected to a computer over a connection medium such as a bus, crossbar, network, or other interconnect. In addition, embodiments can be used to store a file on a remote server or on a storage device accessible to the remote server.

Furthermore, cloud computing is another example where files are often stored on remote servers or remote storage systems. Cloud computing refers to pooled network resources that can be quickly provisioned so as to allow for easy scalability. Cloud computing can be used to provide software-as-a-service, platform-as-a-service, infrastructure-as-a-service, and similar features. In a cloud computing environment, a user may store a file in the "cloud," which means that the file is stored on a remote network resource though the actual hardware storing the file may be opaque to the user.

Figure 1B:
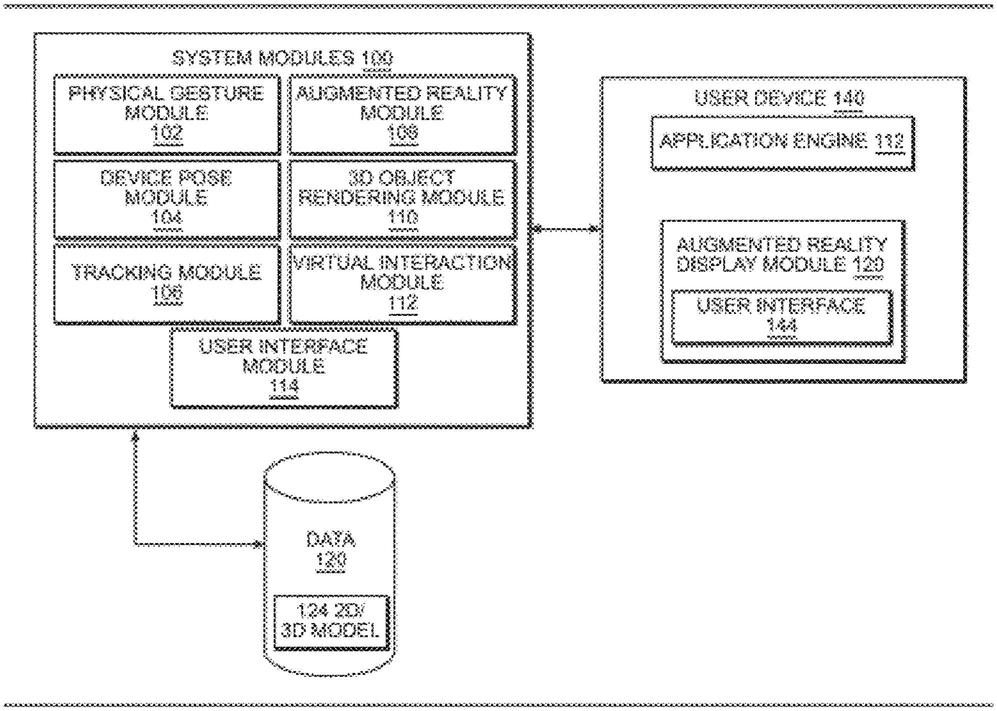
FIG. 1B is a block diagram illustrating an exemplary computer system that performs augmented reality (AR) processing according to example embodiments.

FIG. 1B illustrates a block diagram of an example system 100 that performs AR processing and which includes a physical gesture module 102, a device pose module 104, a tracking module 106, an AR module 108, a 3D object rendering module 110, a virtual interaction module 112 and a user interface module 114. The system 100 may communicate with a user device 140 to display output, via a user interface 144 generated by an application engine 142. In various embodiments, the user device 140 may be an AR display headset device that further includes one or more of the respective modules 102, 104, 106, 108, 110, 112, 114. The user device 140 may also be a display module that illustrates a live selection made by a hand-held instrument and/or probe brought near an area of a patient and which may include a virtual tip or extension that appears to enter the body on the display but which is not actually touching the patient body.

The physical gesture module 102 of the system 100 may perform functionality, steps, operations, commands and/or instructions as illustrated in one or more of FIGS. 2A, 2B, 2C, 2D, 2E, 2F, 2G, 2H, 3A, 3B, 4 and 5, ("FIGS. 2A-5").

The device pose module 104 of the system 100 may perform functionality, steps, operations, commands and/or instructions as illustrated in one or more of FIGS. 2A-5.

The tracking module 106 of the system 100 may perform functionality, steps, operations, commands and/or instructions as illustrated in one or more of FIGS. 2A-5.

The augmented reality module 108 of the system 100 may perform functionality, steps, operations, commands and/or instructions as illustrated in one or more of FIGS. 2A-5.

The 3D object rendering module 110 of the system 100 may perform functionality, steps, operations, commands and/or instructions as illustrated in one or more of FIGS. 2A-5.

The virtual interaction module 112 of the system 100 may perform functionality, steps, operations, commands and/or instructions as illustrated in one or more of FIGS. 2A-5.

The user interface module 114 of the system 100 may perform functionality, steps, operations, commands and/or instructions as illustrated in one or more of FIGS. 2A-5.

A database 120 associated with the system 100 maintains information, such as 3D medical model data 124, in a manner the promotes retrieval and storage efficiency and/or data security. In addition, the model data 124 may include rendering parameters, such as data based on selections and modifications to a 3D virtual representation of a medical model rendered for a previous Augmented Reality (AR) display. In various embodiments, one or more rendering parameters may be preloaded as a default value for a rendering parameter in a newly initiated session of the interaction module 112, such as for an ultrasound procedure.

In various embodiments, the interaction module 112 accesses one or more storage locations that contain respective portions of medical model data 124. The medical model data 124 may be represented according to two-dimensional (2D) and three-dimensional (3D) medical model data. The 2D and/or 3D ("2D/3D") medical model data 124 may include a plurality of slice layers of medical data associated with external and internal anatomies. For example, the 2D/3D medical model data 124 may include a plurality of slice layers of medical data for generating renderings of external and internal anatomical regions of a user's head, brain, urinary tract, stomach, limbs, reproductive organs and skull. It is understood that various embodiments may be directed to generating displays of any internal or external anatomical portions of the human body and/or animal bodies.

The interaction module 112 may render the 3D virtual medical model in an AR display based on the 3D medical model data. In addition, the interaction module 112 renders the 3D virtual medical model based on model pose data which describes an orientation and position of the rendering of the 3D virtual medical model. The interaction module 112 applies the model pose data to the 3D medical model data to determine one or more positional coordinates in the unified 3D coordinate system for portion(s) of model data of a slice layer(s) that represent various anatomical locations.

The interaction module 112 further renders the 3D virtual medical model based on a current device pose of an AR headset device worn by the user. The current device pose represents a current position and orientation of the AR headset device in the physical world. The interaction module 112 translates the current device pose to a position and orientation within the unified 3D coordinate system to determine the user's perspective view of the AR display. The interaction module 112 generates a rendering of the 3D virtual medical model according to the model pose data for display to the user in the AR display according to the user's perspective view. Similarly, the interaction module 112 generates instrument pose data based on a current pose of a physical instrument. The current instrument pose represents a current position and orientation of a physical instrument in the physical world. For example, the physical instrument may be held by a user's hands and may have one or more fiducial markers. The interaction module 112 translates the current instrument pose to a position and orientation within the unified 3D coordinate system to determine the physical instrument's display position and orientation in the AR display and/or placement with respect to one or more virtual objects. It is understood that the interaction module 112 continually updates the instrument pose data to represent subsequent changes in the position and orientation of the physical instrument.

Various embodiments described herein provide functionality for selection of menu functionalities and positional display coordinates. For example, the interaction module 112 tracks one or more physical gestures such as movement of a user's hand(s) and/or movement of a physical instrument(s) via one or more tracking algorithms to determine directional data to further be utilized in determining whether one or more performed physical gestures indicate a selection of one or more types of functionalities accessible via the AR display and/or selection and execution of a virtual interaction(s). For example, the interaction module 112 may track movement of the user's hand that results in movement of a physical instrument and/or one or more virtual offsets and virtual objects associated with the physical instrument. The interaction module 112 may determine respective positions and changing positions of one or more hand joints or one or more portions of the physical instrument. In various embodiments, the interaction module 112 may implement a simultaneous localization and mapping (SLAM) algorithm.

The interaction module 112 may generate directional data based at least in part on average distances between the user's palm and the user's fingers and/or hand joints or distances between portions (physical portions and/or virtual portions) of a physical instrument. In some embodiments, the interaction module 112 generates directional data based on detected directional movement of the AR headset device worn by the user. The interaction module 112 determines that the directional data is based on a position and orientation of the user's hand(s) (or the physical instrument) that indicates a portion(s) of a 3D virtual object with which the user seeks to select and/or virtually interact with and/or manipulate.

According to various embodiments, the interaction module 112 may implement a collision algorithm to determine a portion of a virtual object the user seeks to select and/or virtually interact with. For example, the interaction module 112 may track the user's hands and/or the physical instrument according to respective positional coordinates in the unified 3D coordinate system that correspond to the orientation of the user's hands and/or the physical instrument in the physical world. The interaction module 112 may detect that one or more tracked positional coordinates may overlap (or be the same as) one or more positional coordinates for displaying a particular portion(s) of a virtual object. In response to detecting the overlap (or intersection), the interaction module 112 determines that the user seeks to select and/or virtually interact with the portion(s) of the particular virtual object displayed at the overlapping positional coordinates.

According to various embodiments, upon determining the user seeks to select and/or virtually interact with a virtual object, the interaction module 112 may detect one or more changes in hand joint positions and/or physical instrument positions and identify the occurrence of the position changes as a performed selection function. For example, a performed selection function may represent an input command to the interaction module 112 confirming the user is selecting a portion of a virtual object via a ray casting algorithm and/or collision algorithm. For example, the performed selection function may also represent an input command to the interaction module 112 confirming the user is selecting a particular type of virtual interaction functionality. For example, the user may perform a physical gesture of tips of two fingers touching to correspond to a virtual interaction representing an input command, such as a select input command.

The interaction module 112 identifies one or more virtual interactions associated with the detected physical gestures. In various embodiments, the interaction module 112 identifies a virtual interaction selected by the user, or to be performed by the user, based on selection of one or more functionalities from a 3D virtual menu displayed in the AR display. In addition, the interaction module 112 identifies a virtual interaction selected by the user according to one or more pre-defined gestures that represent input commands for the interaction module 112. In some embodiments, a particular virtual interaction may be identified based on a sequence of performed physical gestures detected by the interaction module 112. In some embodiments, a particular virtual interaction may be identified as being selected by the user based on a series of preceding virtual interactions.

Various embodiments herein may include a method(s), computer program code or computer system(s) for defining a display position of an image plane proximate to a current position of an ultrasound probe instrument. A calibration selection corresponds to ultrasound imagery depth. The calibration selection may be based on an assignment of a measure of distance per pixel of the situated view. An Augmented Reality (AR) situated view is rendered on the image plane. The AR situated view portrays ultrasound imagery captured by the ultrasound probe instrument.

An AR display orientation of the image plane, displayed at the display position, is based on one or more detected movements of an AR headset. A first display orientation of the image plane is based on a current position and orientation of an AR headset device. A second display orientation of the image plane is based on one or more changes to the position and orientation of an AR headset device.

First ultrasound image content is rendered and portrayed by the situated view on the image plane while the image plane is displayed at the first display position. The first display position of the image plane and the first ultrasound image content correspond to a first position of the ultrasound probe instrument. The image plane may also be displayed according to a first image plane display orientation. The first image plane display orientation is based on a current position and orientation of the AR headset-instead of the first position of the ultrasound probe instrument The same first ultrasound image content is rendered and portrayed by the situated view on the image plane while the image plane is displayed first display position of the image plane—but the orientation of the image plane may have been subsequently changed according to a second image plane display orientation. The first display position of the image plane and the first ultrasound image content stills correspond to the first position of the ultrasound probe instrument. However, the image plane is oriented according to the second image plane display orientation, which corresponds to one or more changes to the current position and orientation of an AR headset device.

Second ultrasound image content is rendered and portrayed by the situated view at a second display position of the image plane. The second display position of the image plane and the second ultrasound image content correspond to a subsequent second position of the ultrasound probe instrument. The second display orientation of the image plane is maintained as the situated view updates the portrayal of the first ultrasound image content with portrayal of the second ultrasound image content-due to lack of a change to the position and orientation of the AR headset.

Figure 2A:
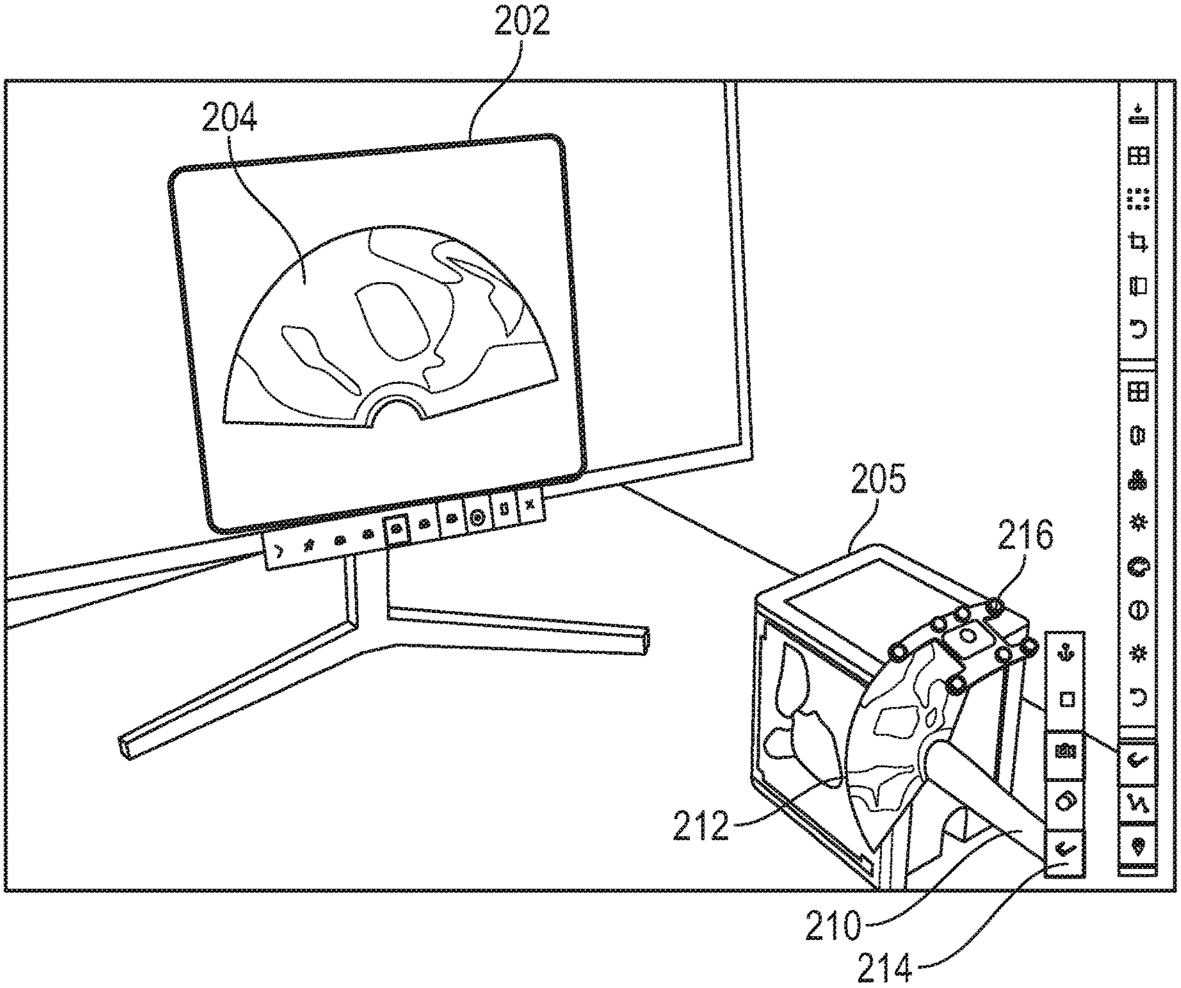
FIG. 2A illustrates an AR viewing environment with an ultrasound device during an ultrasound procedure according to example embodiments.

FIG. 2A illustrates an AR viewing environment with an ultrasound device during an ultrasound procedure according to example embodiments. Referring to FIG. 2A, the user of the headset may be able to view content as provided by the example in FIG. 2A. The view may be an augmented reality (AR) view where objects in the room are present as well as overlaid user interfaces, such as display area 202 which includes a projection view of an ultrasound 204 as conducted by an ultrasound device 210.

It is understood that embodiments described here are intended to be performed with respect to an actual patient's internal anatomy. Patient anatomy may modeled by a trainer box 205, which includes artificial skin and organs used to simulate a human's internal anatomy around an orifice, such as a throat, vagina, anal cavity, etc. The trainer box also includes nearby organs. It is understood that embodiments described herein function and perform in the same manner when the sensor 216 is placed in, near and/or over a portion of an actual patient's physical anatomy. As such, the trainer 205 will be referred to as the 'patient' and will include an opening to represent a bodily orifice, an internal organ(s) or any portion of internal anatomy, all of which can be detected by the ultrasound device probe 210.

Figure 2B:
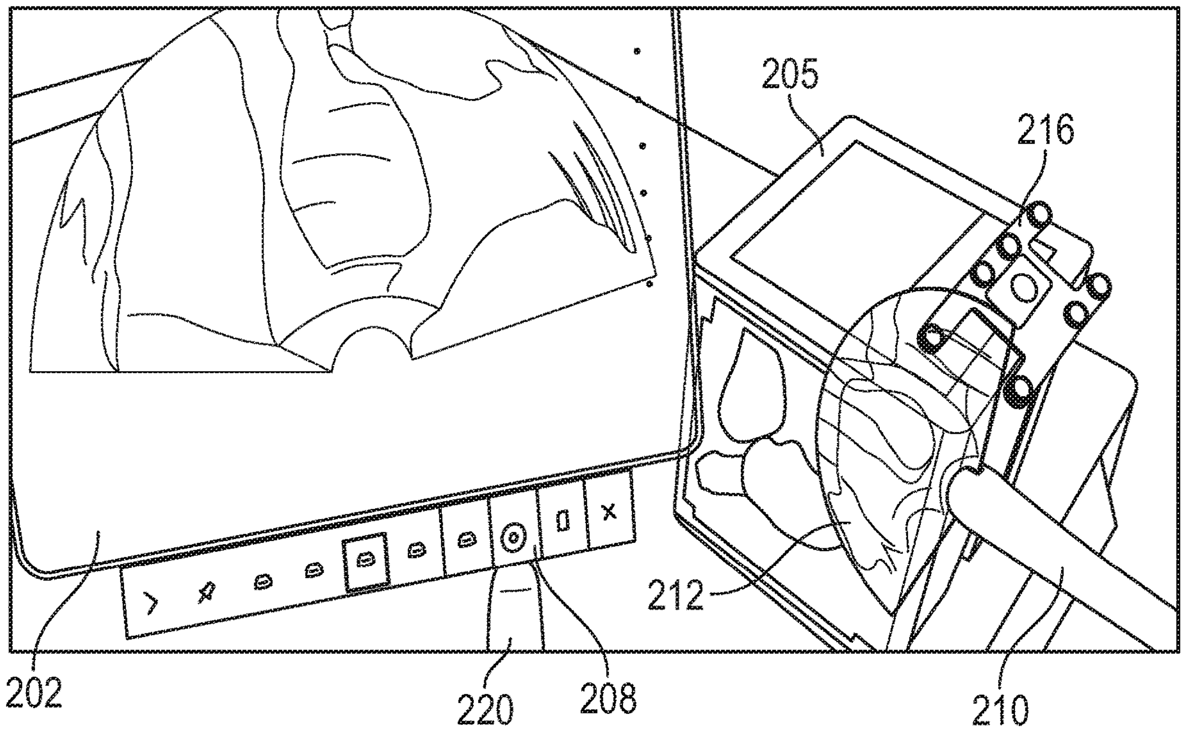
FIG. 2B illustrates conducting an image capture in an AR viewing environment with an ultrasound device during an ultrasound procedure according to example embodiments.

The sensor 216 may be placed on top of the patient body (see 'trainer' box 205) and be used as a point of reference distance to the probe 210. The projected ultrasound can be viewed as a planar sample of the patient depending on the angle and location of the probe tip 210. The planar sample may be viewed at the location of the ultrasound 212 and on a virtual display area 202 as a single sample 204. The virtual buttons 208 on the display 220 may be selected by the user's finger 220 as illustrated in FIG. 2B. One option would be to save the image as an ultrasound image as part of an ultrasound ordered by a medical professional. The AR display as illustrated in FIG. 2A may include virtual buttons on the side of the viewing area 214 as well as on the main virtual display area 202.

FIG. 2B illustrates conducting an image capture in an AR viewing environment with an ultrasound device during an ultrasound procedure according to example embodiments. Referring to FIG. 2B, the view of the virtual display area 202 includes an example where a user's finger is selecting a virtual object rendered as a selectable menu option 208 to record the image as part of an ultrasound procedure which may include various images at various angles and depths as measured by the probe 210. The probe 210 may be an ultrasound probe instrument.

Ultrasound imaging brings about a challenge in being able to easily identify what exactly is being viewed at any given time. The purpose of an ultrasound may be to provide still images of a localized portion of a user's anatomy, such as the area around the prostate gland. The scanning process performed by a technician is manually performed by a probe being aligned to the person's body and in some cases, inserted into a bodily orifice in order to obtain a closer internal view of, for example, the prostrate, urethra, and/or bladder which are all near the same area in a male patient. Most ultrasounds are performed by a skilled technician with experience and training. Others may not be confident performing such a task if their experience is limited. The AR configuration of the various embodiments offers a simpler and more adaptable approach to performing and completing an ultrasound.

An ultrasound is often performed by an anatomical surface measurement device, such as a probe 210, which can be inserted into a bodily orifice. Other types of ultrasound devices may rest on the surface of the patient's skin. When operating the probe 210, it may be difficult to visualize ultrasound imagery at correct depths and angles necessary to satisfy the criteria for the parties that are tasked with interpreting ultrasound data to make a decision regarding the likelihood of a foreign body growth, such as an enlarged organ, etc.

According to various embodiments, initiating the ultrasound over the cavity of the patient 205 via the probe 210 provides an AR situated view 212 proximate to the tip of the probe 210. The term 'proximate' may be considered near, touching, and may also be representative of an area that is contiguous with a virtual portion of the probe identified by the AR headset and software application instead of a mere physical portion of the probe. The user may have limited experience with understanding the angle and orientation of the probe with respect to a current physical orientation of internal organs. Various embodiments generate the situated view 212 in order to assist a user in assessing whether the probe 210 should be rotated and/or moved backward or forward in a three-dimensional space to identify the anatomical areas of the patient via ultrasound imaging. A user can see exactly where they are scanning and any angular inclination is observable when using the AR headset.

The AR headset worn by the user may also permit the increase/decrease in ultrasound depth to capture ultrasound images at various depths within the patient's anatomy. The AR headset provides users with the ability to control ultrasound settings directly from an AR display interface 202 rendered via the AR headset. The same rendering of the situated view 212 is displayed for the user when the user moves from the right of the patient to the left of patient—while holding the probe 210. This enables a user to be located at any perspective position and still be able to view the same ultrasound imagery portrayed by the situated view 212 regardless of changes of a physical orientation of the AR headset due to movement of the user.

Embodiments herein generate and render a virtual object as a sensor 216. The sensor 216 provides a point of reference with respect to a current physical orientation of the patient body and a current physical orientation of the probe 210. The headset position and the ultrasound device position are trackable and may therefore be known at all times, and the sensor 216 displayed as an overlay with respect to a surface of the patient 205 may provide a consistent and efficient view of the anatomical structure of the physical area being examined.

Once the ultrasound data is obtained via the probe 210, the ultrasound data may be mapped to a three-dimensional coordinate system that is shared with the headset. In operation, a current position and orientation of the probe 210 is continually tracked and detected relative to continuous changes in the position and orientation of the headset within the coordinate system. Various embodiments perform a mapping process via identifying pixels of image data as captured by the probe 210 and determining distances, such as a number of millimeters each pixel represents (Dp), distances between the pixels (Dbp), distances with respect to the pixels and the sensor 216 (Ds) and applying those various distances to create a live image of the detected content associated with the patient.

When the headset is moved from a first position to a second position, the same image content may be identified from the headset viewer as an AR overlay of image data portrayed in the situated view 212. In one example, as the headset moves from the first position to the second position and the ultrasound probe 210 is kept in a same physical orientation near or inside a patient, the situated view 212 maintains the same AR ultrasound image content-regardless of the headset's movement. From the headset perspective, the AR ultrasound image content is adjusted to stay in the same position, such as near the patient body, upright and without moving up or down and side to side. That is, a plane of the situated view 212 is adjusted so that it can be viewed by a user wearing a headset based on changes to the current position and physical position of the headset—but the ultrasound image portrayed within the situated view 212 is not impacted by the headset's movement. The ultrasound image portrayed by the situated view 212 is updated based on a current position and physical orientation of the probe 210 and subsequent changes to the probe's 210 respective positions and physical orientations. For example, in various embodiments, if a user wearing the headset moves from a first perspective view from above a front side of the patient to a second perspective view that makes the back side of the patient visible, the planar positioning of the situated view 212 would be adjusted based on movement of the headset—but the ultrasound imagery portrayed by the situated view 212 would be modified based on changes of the position and physical orientation of the probe 210 independent of any detected movement of the headset.

In various embodiments, the ultrasound imagery displayed in the situated view 212 near the tip of the probe 210 may be a cross-section of the anatomical structure of the patient a set distance away from the tip of the probe 210, which enables the probe to provide a preview of the patient anatomy without even being inserted into a body cavity/orifice. The setting of the ultrasound preview may specify a number of inches or centimeters desired to be identified as at any given time (see FIGS. 3A and 3B). The user can essentially virtually 'cut' the patient at one spot and view the cross-section of the patient in real time prior to selecting an image as relevant and storing the data as part of an ultrasound file of various images indicating various depths and angles of the patient.

The situated perspective permits the user to view how the ultrasound image changes in relation to movement of the of the instrument, which may include different tissue densities and masses. A first depth of the instrument may be outside the patient body which may not include a view of the bladder which is further inside the patient, so the depth of instrument's virtual detection capabilities and/or the depth position of the instrument inside the patient may permit a view of the bladder. A different depth or movement up, down, right or left may provide a view of more internal organs that are closer to those positions. The previewed data that is viewable at all times will enable the technician to more easily view other anatomical structures of the patient easier More or fewer millimeters of ultrasound instrument positioning may be depend on the depth setting of the ultrasound instrument. The perspective view of the user depends on the current ultrasound plane rendering provided by the headset. A correction measure that is applied to the rendering permits the current image to be rendered in a constant physical frame of reference as long as the ultrasound sensor 216 and the probe 210 are maintained in a fixed position, a full visual view of the same medical data is provided according to a set scale and based on where the headset is currently located. The probe 210, sensor 216 and the headset may use a linear transformation to provide such data. A distance setting applied to the pixels of a fraction of a millimeter, may be used to maintain the transformation between pixels, such as, 2 microns or a similar distance. Such a distance setting can be used as the basis for the linear transformation of image data to visualization data viewable via the AR headset.

According to various embodiments, a virtual sensor ("sensor") may be concurrently displayed with the situated view in the AR environment. The sensor may also be an overlay displayed proximate to a patient and have its position defined according to the unified three-dimensional (3D) coordinate system. As such, respective positions in 3D space of the sensor and probe can be continuously tracked and known. The sensor and probe thereby provide known reference positions with respect to the position and physical orientation of the patient, while the situated view displays ultrasound imagery visualized via the probe, and the positioning of the situated view's image plane adjusts according to movement of the headset.

Various embodiments utilize the reference positions of the sensor and probe and the calibration (i.e., pixels per distance) for performance of a liner transformation algorithm to determine a display position of the situated view's image plane that is proximate to the probe's tip. Various embodiments may include a 3D medical model of the patient's anatomy and may provide for registering portions of the 3D medical model with the ultrasound imagery portrayed in the situated view. The 3D medical model may be portrayed as a virtual object in the AR environment that can be moved and manipulated in response to physical gestures applied to the virtual object.

In some embodiments, the 3D medical model may represent internal anatomy that is being visualized in the situated view via the probe. The user may perform respective physical gestures thereby adjusting a display position of the 3D medical model in the AR environment that results in aligning the visualization of the internal anatomy offered by the 3D medical model with real-time ultrasound imagery of the same internal anatomy portrayed in the situated view. Once the 3D medical model appears to the user as visually aligned in the AR environment with the depiction of the same internal anatomy shown in the situated view, the user may select to register the current position and physical orientation of the 3D medical model.

According to various embodiments, once the 3D medical model is registered, the position and physical orientation of the probe may still change in response to how it is being handled by the individual manually controlling the probe. The situated view may thereby be updated to portray changes in the ultrasound imagery that correspond to changes to the position and physical orientation of the probe. Since positions of the situated view and the registered 3D medical model are known according to the unified 3D coordinate system, collisions between portions of the situated view and portions of the registered 3D medical model may be detected as the probe is physically moved. Those portions of the ultrasound imagery in the situated view that collide with the registered 3D medical model may be obscured so as to prioritize display in the AR environment of the visualization of the internal anatomy provided by the registered 3D medical model. Content of the registered 3D medical model may be prioritized over the content of the ultrasound imagery. This approach enables the registered 3D medical model to be displayed while the ultrasound imagery is obscured.

Figure 2C:
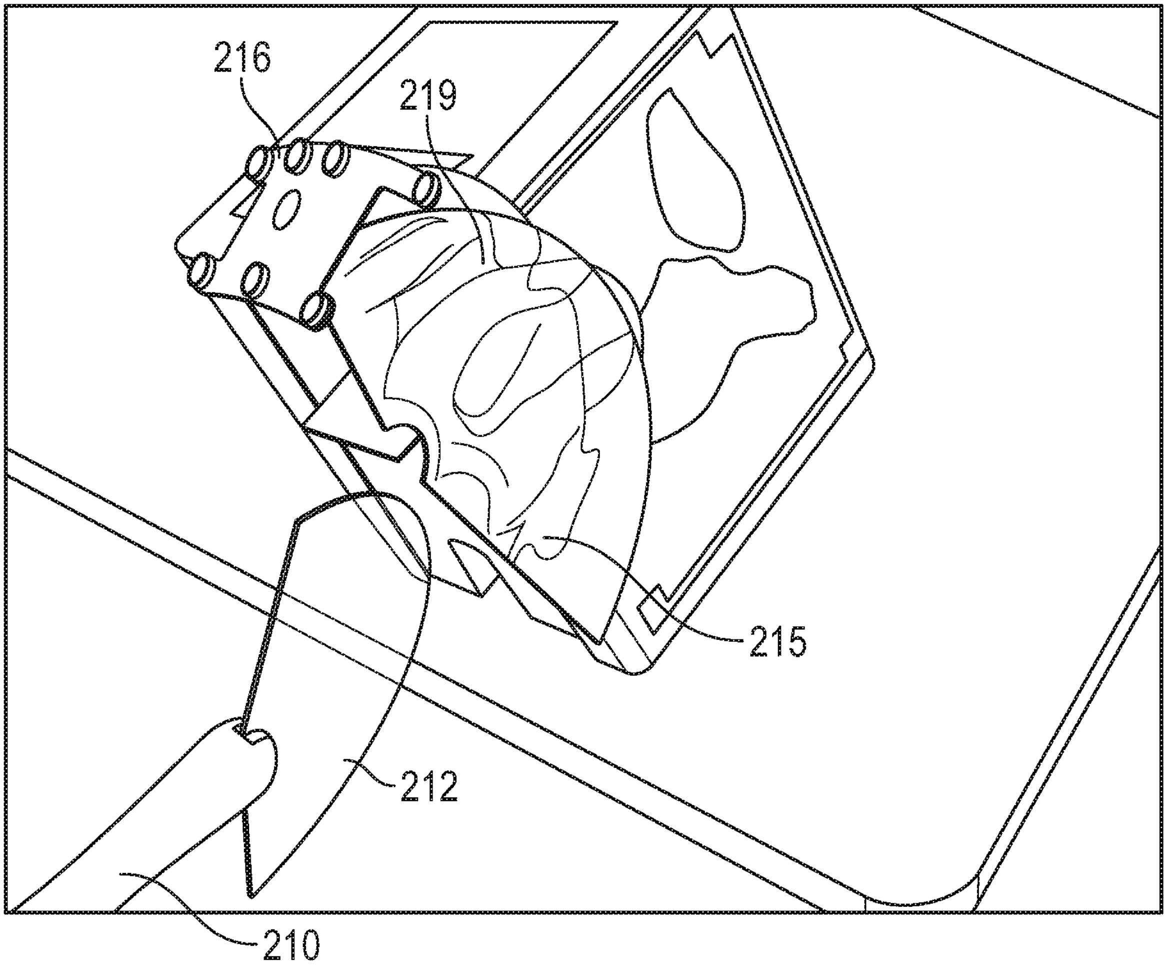
FIG. 2C illustrates multiple images being displayed in an AR viewing environment operating with an ultrasound device during an ultrasound according to example embodiments.

FIG. 2C illustrates multiple images being displayed in an AR viewing environment operating with an ultrasound device during an ultrasound according to example embodiments. Referring to FIG. 2C, the example includes multiples cross-sectional images being overlaid onto the patient. The sensor 216 is placed over the patient area and provides a fixed location where the image data may be captured and maintained over the course of an ultrasound procedure. The probe 210 has a preview area 212 which was used to identify the various images 215 and 219 at varying angles and positions of the probe. The virtual image selection option may have been selected by the user or may be performed autonomously based on a preset time (e.g., every 'X' seconds). Having the images overlaid onto the patient anatomical area provides a way to determine which angles and depths have already been identified and saved to memory.

Figure 2D:
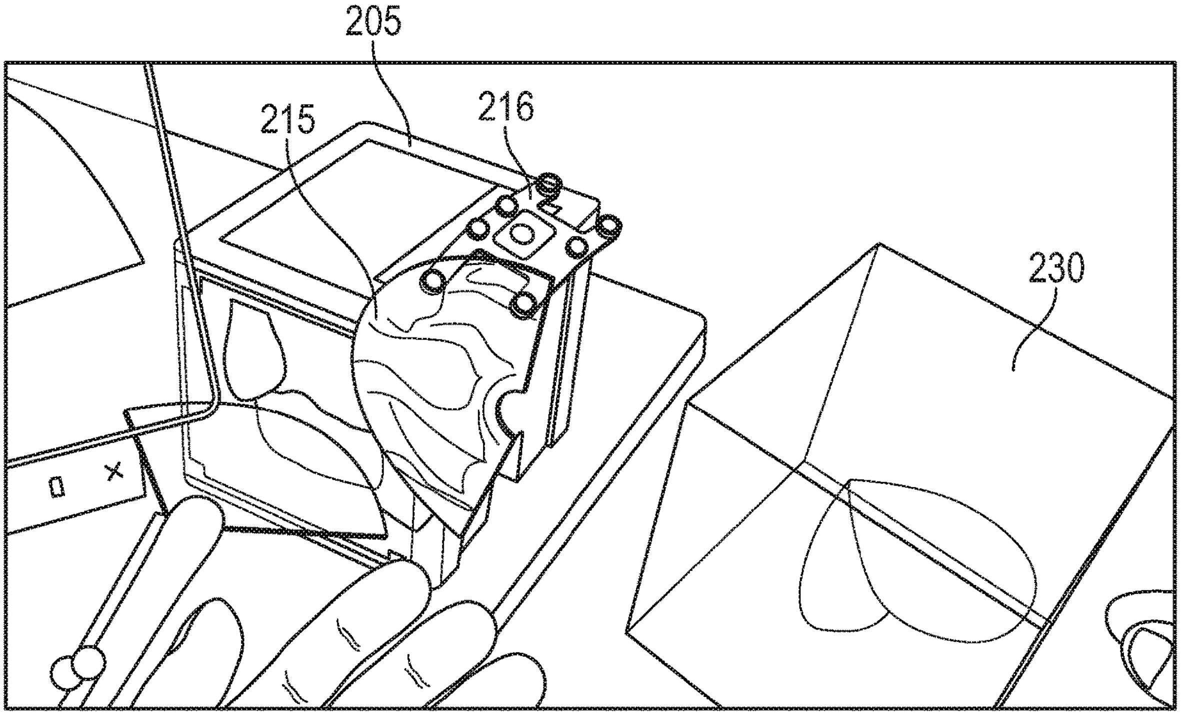
FIG. 2D illustrates multiple images being displayed in an AR viewing environment operating with a situated display perspective according to example embodiments.

FIG. 2D illustrates multiple images being displayed in an AR viewing environment operating with a situated display perspective according to example embodiments. Referring to FIG. 2D, the reference 'box' 230 is shaped the same as the patient 'trainer' box and provides a reference for data to be provided and merged with the patient 205. The user may manipulate the position of the reference 230 via hands and fingers to place the reference 230 over and/or near the box to maintain another point of reference to illustrate which images have been captured so the quantity and quality of the images can be viewed for a level of completeness of the ultrasound procedure.

Figure 2E:
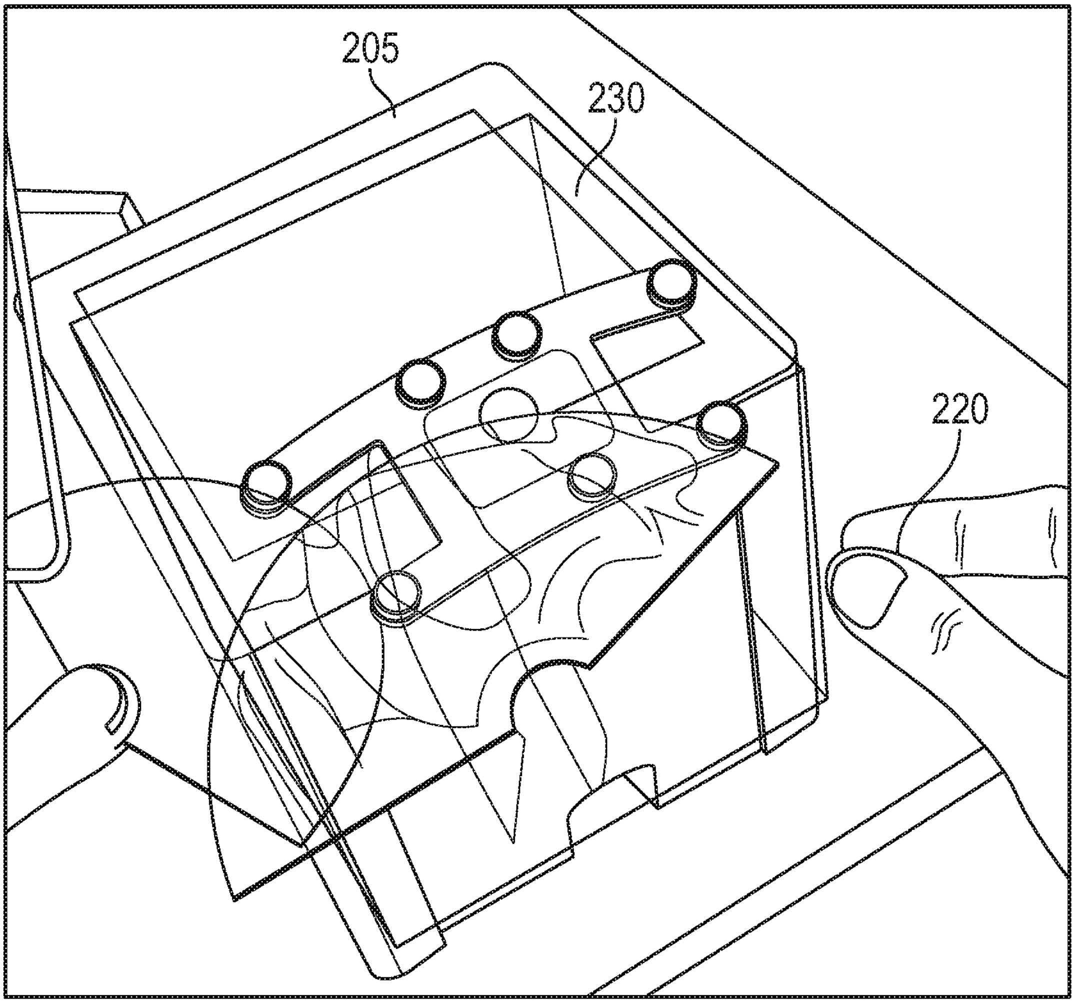
FIG. 2E illustrates multiple images being displayed in an AR viewing environment operating with a situated display perspective being overlaid on the patient space according to example embodiments according to example embodiments.

FIG. 2E illustrates multiple images being displayed in an AR viewing environment operating with a situated display perspective being overlaid on the patient space according to example embodiments according to example embodiments. Referring to FIG. 2E, the reference 230 is placed in the same position as the patient trainer box 205 as a way to merge data that may be necessary for conducting the ultrasound. For example, the reference 230 may include various points in a three-dimensional space where a user will need to identify still frames from the ultrasound device in order to complete the ultrasound procedure.

Figure 2F:
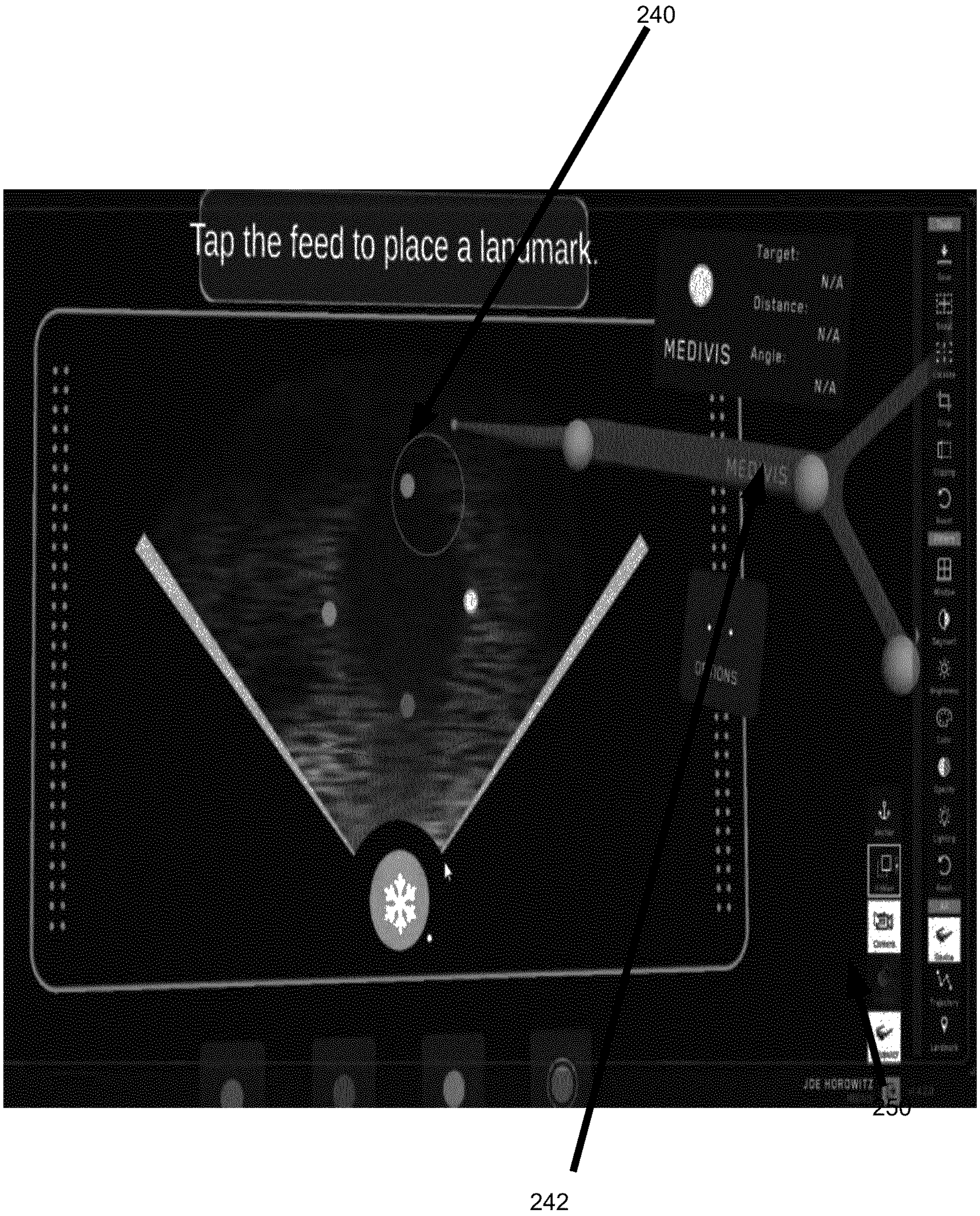
FIG. 2F illustrates a virtual user interface with an ultrasound image being displayed for selection purposes in an AR viewing environment according to example embodiments according to example embodiments.

FIG. 2F illustrates a virtual user interface with an ultrasound image being displayed for selection purposes in an AR viewing environment according to example embodiments according to example embodiments. Referring to FIG. 2F, a virtual selection instrument 242 is illustrated as being used to select locations 240 (dots, coordinates) on a two-dimensional image as points of interest. Such as those surrounding anatomical image of a patient's prostrate. The target dots 240 may be different colors and/or shades to identify unique locations where the image data is needed.

Figure 2G:
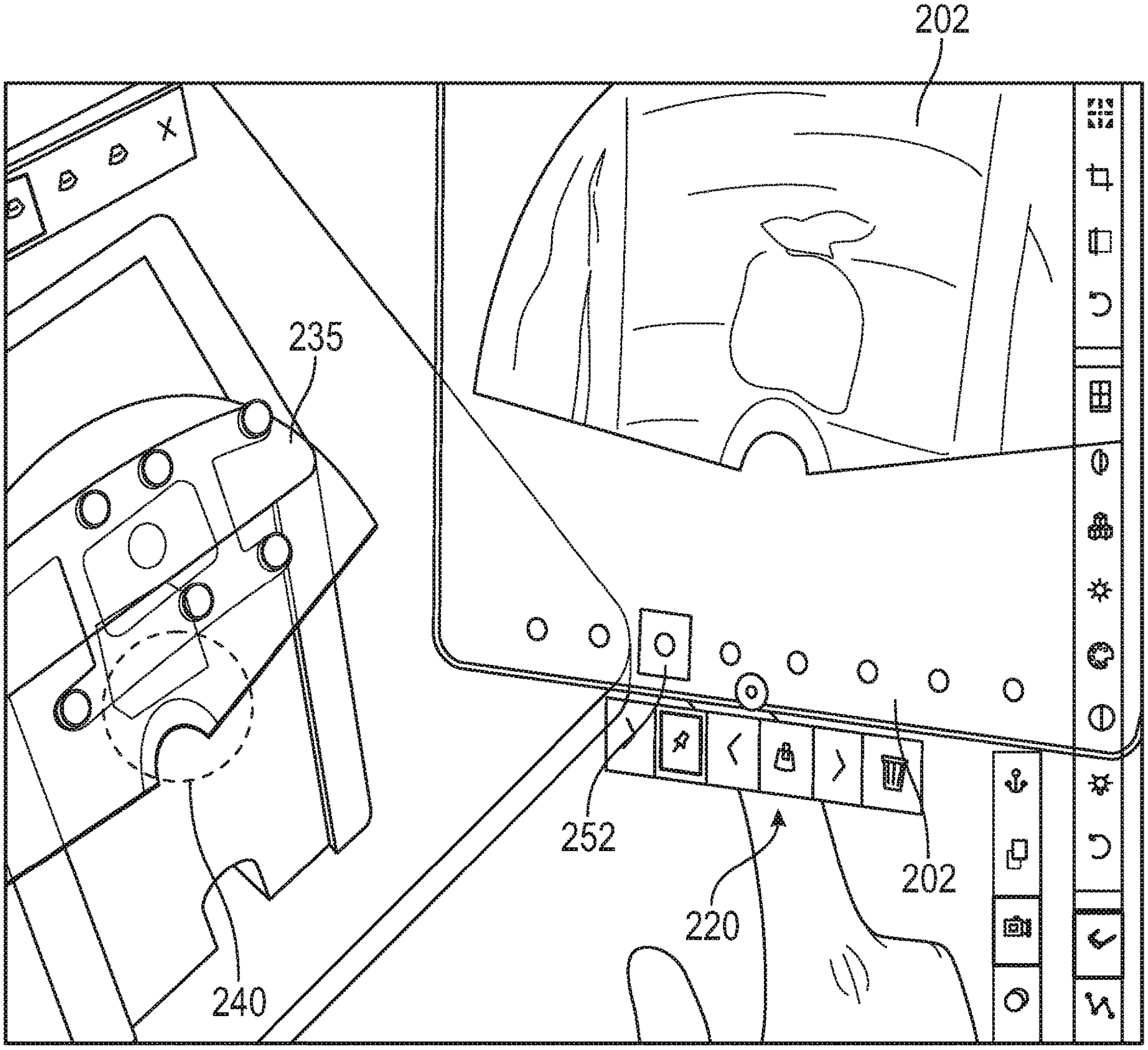
FIG. 2G illustrates a virtual user interface with one or more reference points being displayed on the patient space in an AR viewing environment according to example embodiments according to example embodiments.

FIG. 2G illustrates a virtual user interface with one or more reference points being displayed on the patient space in an AR viewing environment according to example embodiments according to example embodiments. Referring to FIG. 2G, the display area 202 illustrates a cross-sectional view of anatomical data with options to select a colored dot 252 to be placed on the display via a handheld selection tool and/or a user finger 220 when the locations of interest 240 are identified at the patient via a set of location data 235 that is placed on the patient. The dots in the example 240 are selected to be as close as possible to the target dots and a same color may be used to identify the pairings of targets dots vs. actual selected dots.

Figure 2H:
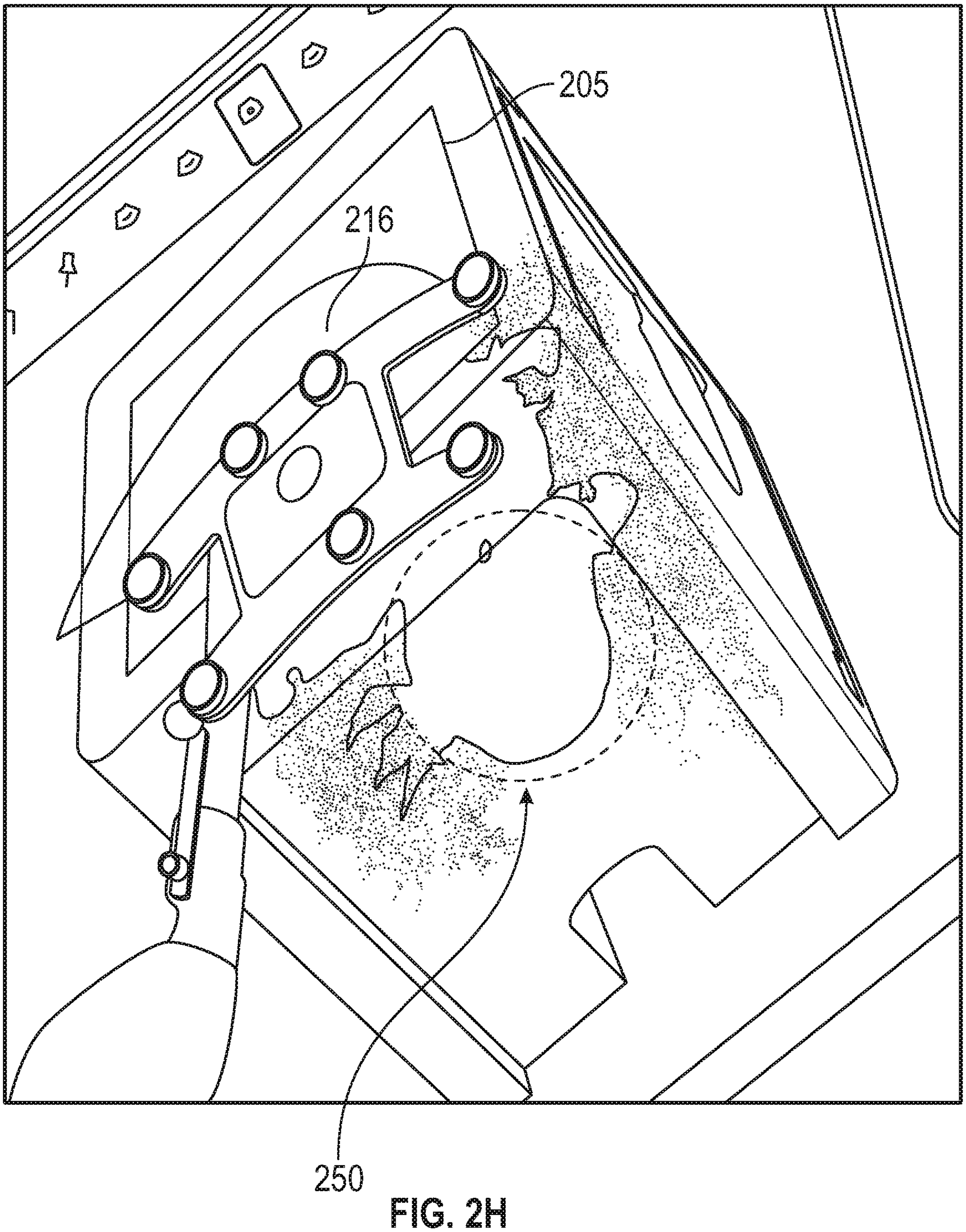
FIG. 2H illustrates a virtual user interface with one or more reference points and one or more selected points being displayed on the patient space in an AR viewing environment according to example embodiments according to example embodiments.

FIG. 2H illustrates a virtual user interface with one or more reference points and one or more selected points being displayed on the patient space in an AR viewing environment according to example embodiments according to example embodiments. Referring to FIG. 2H, the result of the target locations/dots being overlaid on the patient as reference points and the user selection operations demonstrates pairings 250 of reference points. The exact locations of the dots should be close to provide an accurate ultrasound result at the positions in three-dimensional space where the images are captured.

The result of the ultrasound data may be a direct linear transformation (DLT). The scanner data provides brightness levels depending on reverberance, or reflection of sound, and the ultrasound device will encode that data as a single frame video stream or image plane. In a learning process for the ultrasound, a setting may be adjusted to identify one pixel on the horizontal axis and one pixel on the vertical axis of an image. The transformation is effectively scaling the plane to match the pixel(s). Once the scale is known, the location of the plane with respect to the sensor 216 must also be identified. Depending on the transformation, the center might move up and down, or it might move left and right. The center of the plane needs to be identified with respect to the sensor (i.e., center of sensor). A DLT can then be performed through a calibration process. After identifying the plain size and center, the sensor location and orientation with respect to a marker or tracker must be identified. In this example, an optical (infrared) and/or reflective tracker is used.

All such data may be tracked directly through the headset. The camera on the headset may identify such necessary data or a camera near the location may work as well to track the environment and perform a calibration. The orientation of the headset and the position with respect to the camera and the orientation and position of the tracker with respect to the camera can inform the headset the region viewable by the headset. In one example, a cross-section may be instantiated to illustrate a section of the patient and the right and left sides of the cross-section may be viewable, thus creating a virtual model that is cut in half by the instantiated cross-section. The other organs or portions of the patient may be identifiable by the cross-section and then the ultrasound probe can be used to identify other areas of interest. The cross-sections being identifiable provides a way to quickly identify areas of interest instead of constantly guessing and moving the probe around. The volume area defined by the AR device may be moved aside to illustrate a replica of the ultrasound on one side of the patient without any distractions, which provides a view of the previously collected image(s) and the live image(s). Once a satisfactory representation is registered. The physical coordinates of the ultrasound can be merged with the coordinates in the medical model. In a landmark registration process, a user would collect some points either using a cross-section, such as image slices, or by a manual selection in a three-dimensional space. In the example of a cranial scan, such as a brain scan, landmark points of the face would be collected by a selection process in the AR display. This may include eyes, ears, nose, etc., and when using the pointer instrument which could then be used to provide a three-dimensional transformation.

In the event of performing a targeting process for an internal target(s), such as the patient prostate. the pointer instrument cannot be placed virtually inside the patient to select those points of interest to create a region of interest around the prostate. The situated plane can be used to non-intrusively identify an image slice of that area by a set distance and capture that data as an image plane. Landmarks on this area can be identified and selected as color coded points and as a reference. That ultrasound situated plane can be saved in the reference coordinate system. Then, to transform from a pixel to reference space selections can be made and images can be collected to include the green point, red point, yellow point, etc. The user could select the virtual landmarks on the medical model and then the landmarks on the ultrasound situated display plane. The user would place the same-colored dots at the same locations and register the data at the correct locations. The process can be referred to as aligning the physical landmarks with virtual landmarks selected on the scan. The distance between the locations show the differences after the DLT. The goal is to minimize overall distances between the dots, however, perfection in the selection locations is not necessary.

A similar process can be deployed for needle injections that often require an ultrasound reference. The needle tip may use a calibrated tracker in the AR viewer. The targeting may be performed at a desired location viewable from the ultrasound. The process may use a short axis and an orthogonal long axis representation. The syringe can be aligned with the middle of the sensor. The ultrasound sensor permits an entire view of the syringe and needle location.

Figure 3A:
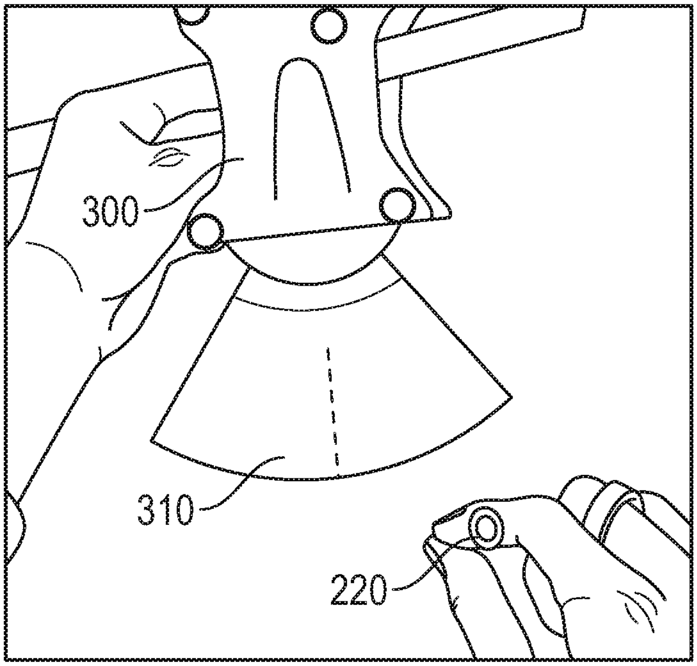
FIG. 3A illustrates a calibration process of selecting an ultrasound depth setting for a selection tool according to example embodiments according to example embodiments.

FIG. 3A illustrates a calibration process of selecting an ultrasound depth setting for a selection tool according to example embodiments according to example embodiments. Referring to FIG. 3A, the calibration instrument or sensor 300 may identify a reference point where an ultrasound plane can be viewable for a preset distance. In this example, the user hand 220 is manipulating a first plane 310 of a viewable area by holding and dragging the plane a first distance as viewed from the AR headset.

Figure 3B:
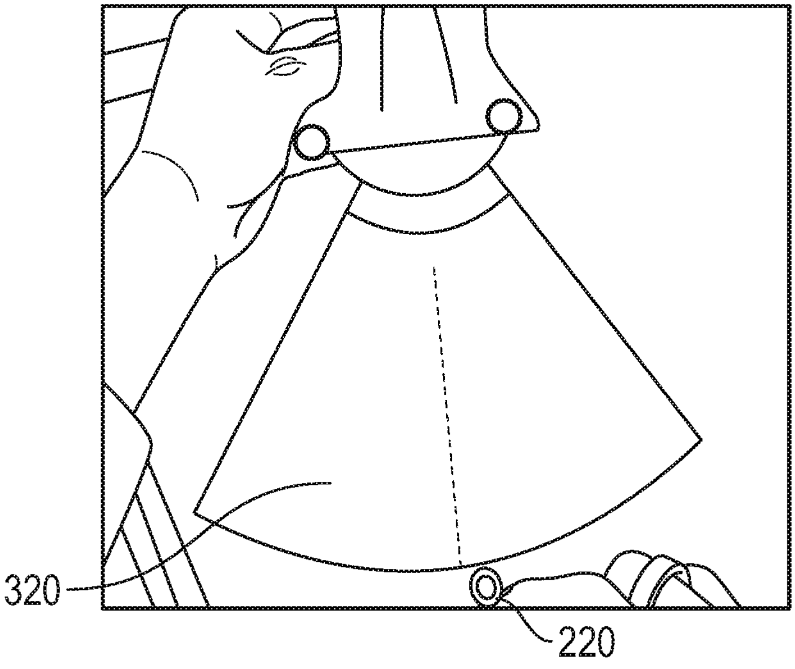
FIG. 3B illustrates a calibration process of selecting a larger ultrasound depth setting for a selection tool according to example embodiments according to example embodiments.

FIG. 3B illustrates a calibration process of selecting a larger ultrasound depth setting for a selection tool according to example embodiments according to example embodiments. Referring to FIG. 3B, the plane distance may be increased 320 by a similar hand gesture or movement. The plane can be customized to any measurable distance from the sensor 300.

Figure 4:
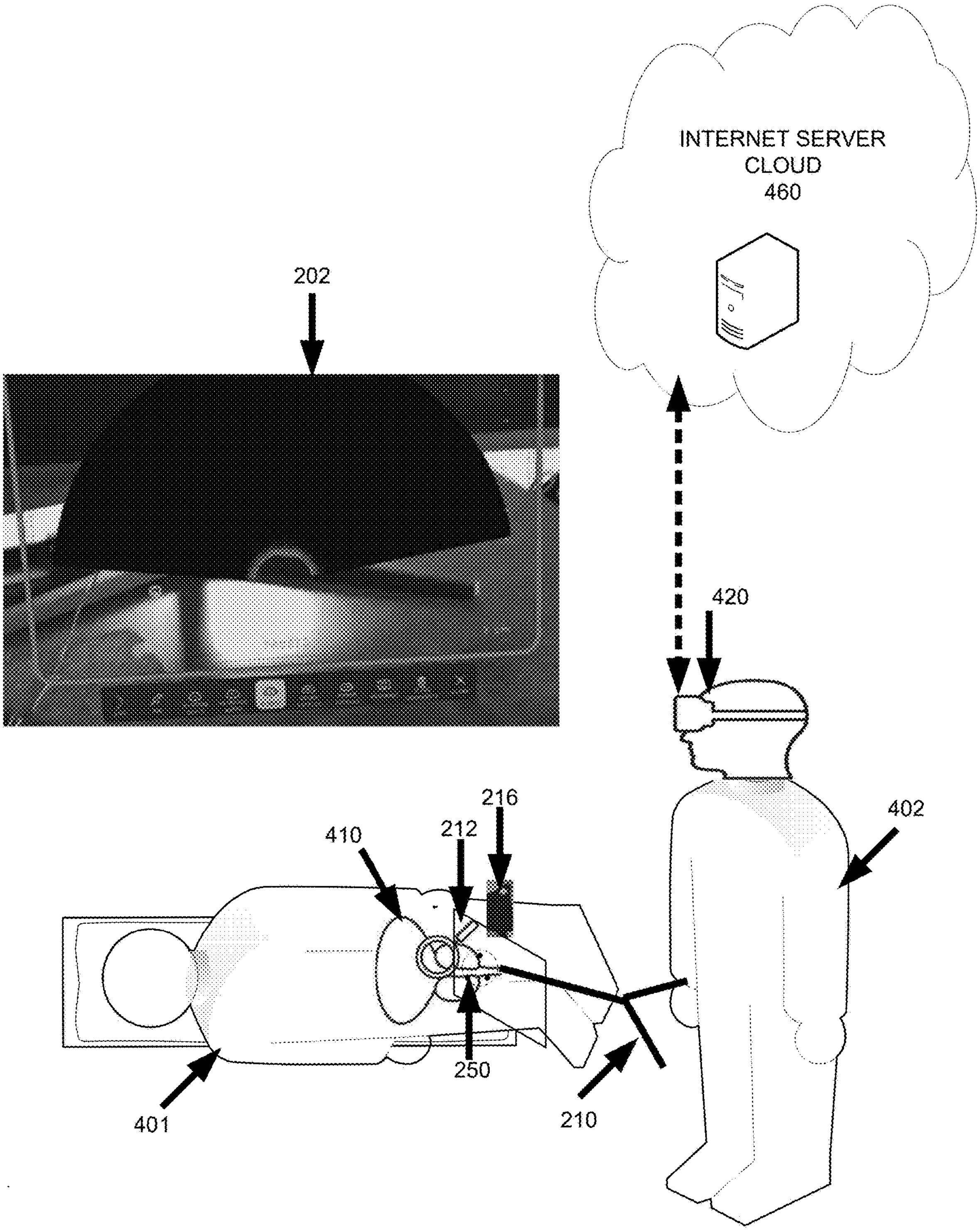
FIG. 4 illustrates network configuration of a live patient being examined according to example embodiments.

FIG. 4 illustrates network configuration of a live patient being examined according to example embodiments. Referring to FIG. 4, the user or ultrasound technician 402 is examining a patient 401 using an AR headset 420 to visualize data associated with the ultrasound probe 210. The probe 210 may identify an ultrasound plane 212 with one or more area of interest, such as landmarks 250 which are specific points which were selected and saved by the technician as viewed through the AR headset 420. The patient is having his prostate and urinary tract area 410 examined by the ultrasound. The planar images detected may be visualized 202 in a virtual interface area which illustrates a planar image captured by the ultrasound probe 210 and based on the sensor 216. The user 402 can view the ultrasound progress, create landmarks and organize images to complete the ultrasound with advanced viewing capabilities offered by the AR headset 420. Data received and stored by the headset 420 may be forwarded to the cloud 460 for storage and retrieval purposes.

Figure 5:
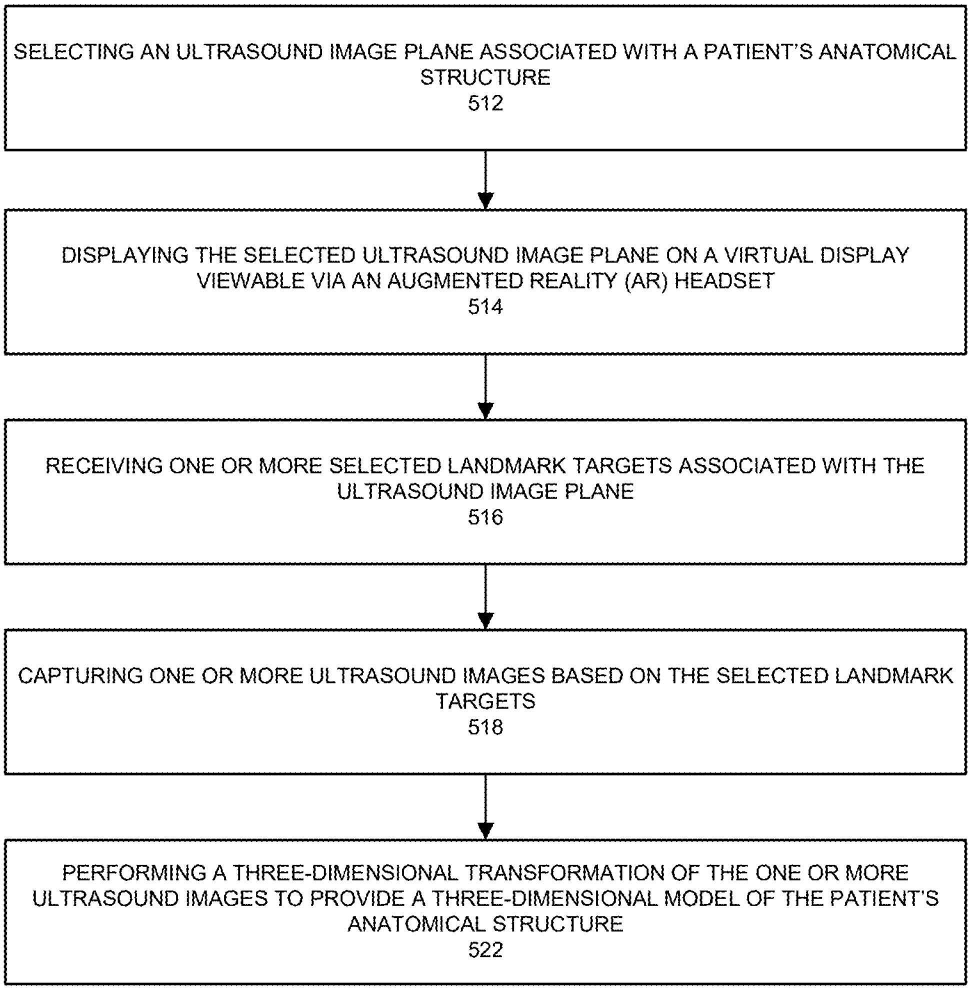
FIG. 5 illustrates an example process according to example embodiments.

FIG. 5 illustrates a flowchart of an example method of operation. Referring to FIG. 5, the process includes selecting, via an ultrasound probe, an ultrasound image plane associated with a patient's anatomical structure 512, displaying the selected ultrasound image plane on a virtual display viewable via an augmented reality (AR) headset 514, receiving one or more selected landmark targets associated with the ultrasound image plane 516, capturing one or more ultrasound images based on the selected landmark targets 518 and performing a three-dimensional transformation of the one or more ultrasound images to provide a three-dimensional model of the patient's anatomical structure 522.

The process may also include identifying a sensor disposed adjacent to the patient's anatomical structure, and virtually overlaying, via the AR headset, the one or more selected landmark targets over the patient's anatomical structure, receiving, via the ultrasound probe, one or more selected landmarks, and displaying the one or more selected landmarks and the one or more selected landmark targets on the virtual display.

The ultrasound image plane may be selected via a non-invasive image capture performed by the ultrasound probe being operated via the AR headset and the receiving the one or more selected landmark targets associated with the ultrasound image plane may include receiving one or more virtual selections on the virtual display. The process may also include capturing a plurality of ultrasound image planes associated with the patient's anatomical structure, and overlaying, via the AR headset, the plurality of ultrasound image planes in a locked position on the patient's anatomical structure, and/or generating, via the AR headset, the ultrasound image plane overlayed on the patient's anatomical structure, and generating, via the AR headset, a replication of the ultrasound image plane away from the patient's anatomical structure.

Although an exemplary embodiment of at least one of a system, method, and non-transitory computer readable media has been illustrated in the accompanied drawings and described in the foregoing detailed description, it will be understood that the application is not limited to the embodiments disclosed, but is capable of numerous rearrangements, modifications, and substitutions as set forth and defined by the following claims. For example, the capabilities of the system of the various figures can be performed by one or more of the modules or components described herein or in a distributed architecture and may include a transmitter, receiver or pair of both. For example, all or part of the functionality performed by the individual modules, may be performed by one or more of these modules. Further, the functionality described herein may be performed at various times and in relation to various events, internal or external to the modules or components. Also, the information sent between various modules can be sent between the modules via at least one of: a data network, the Internet, a voice network, an Internet Protocol network, a wireless device, a wired device and/or via plurality of protocols. Also, the messages sent or received by any of the modules may be sent or received directly and/or via one or more of the other modules.

One skilled in the art will appreciate that a "system" could be embodied as a personal computer, a server, a console, a personal digital assistant (PDA), a cell phone, a tablet computing device, a smartphone or any other suitable computing device, or combination of devices. Presenting the above-described functions as being performed by a "system" is not intended to limit the scope of the present application in any way but is intended to provide one example of many embodiments. Indeed, methods, systems and apparatuses disclosed herein may be implemented in localized and distributed forms consistent with computing technology.

In this specification, reference is made in detail to specific embodiments of the invention. Some of the embodiments or their aspects are illustrated in the drawings.

For clarity in explanation, the invention has been described with reference to specific embodiments, however it should be understood that the invention is not limited to the described embodiments. On the contrary, the invention covers alternatives, modifications, and equivalents as may be included within its scope as defined by any patent claims. The following embodiments of the invention are set forth without any loss of generality to, and without imposing limitations on, the claimed invention. In the following description, specific details are set forth in order to provide a thorough understanding of the present invention. The present invention may be practiced without some or all of these specific details. In addition, well known features may not have been described in detail to avoid unnecessarily obscuring the invention.

Figure 6:
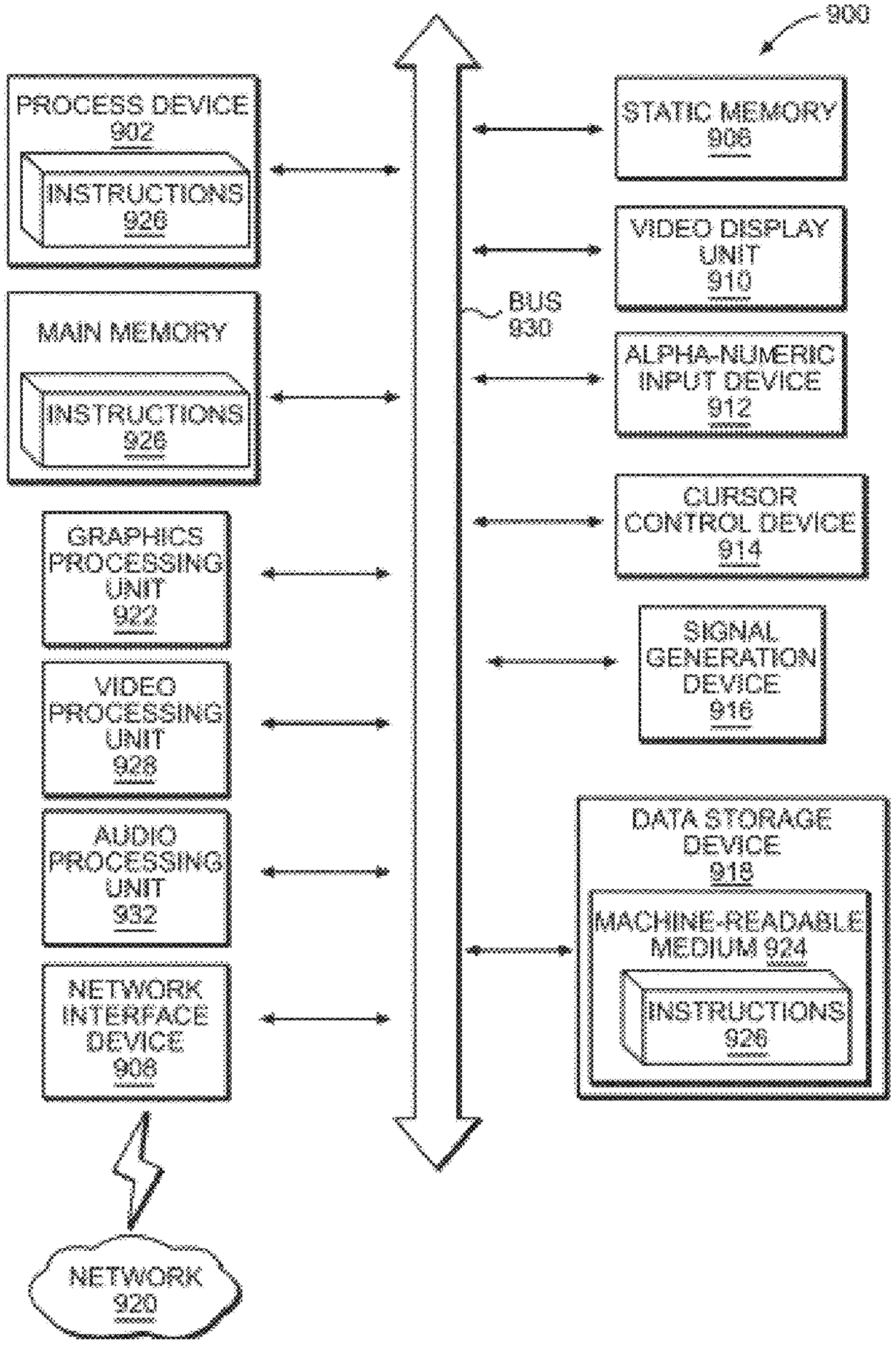
FIG. 6 illustrates an example computing platform used to perform one or more operations associated with example embodiments.

FIG. 6 illustrates an example machine of a computer system within which a set of instructions, for causing the machine to perform any one or more of the methodologies discussed herein, may be executed. In alternative implementations, the machine may be connected (e.g., networked) to other machines in a LAN, an intranet, an extranet, and/or the Internet. The machine may operate in the capacity of a server or a client machine in client-server network environment, as a peer machine in a peer-to-peer (or distributed) network environment, or as a server or a client machine in a cloud computing infrastructure or environment.

The machine may be a personal computer (PC), a tablet PC, a set-top box (STB), a Personal Digital Assistant (PDA), a cellular telephone, a web appliance, a server, a network router, a switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

The example computer system 600 includes a processing device 602, a main memory 604 (e.g., read-only memory (ROM), flash memory, dynamic random access memory (DRAM) such as synchronous DRAM (SDRAM) or Rambus DRAM (RDRAM), etc.), a static memory 606 (e.g., flash memory, static random access memory (SRAM), etc.), and a data storage device 618, which communicate with each other via a bus 630.

Processing device 602 represents one or more general-purpose processing devices such as a microprocessor, a central processing unit, or the like. More particularly, the processing device may be complex instruction set computing (CISC) microprocessor, reduced instruction set computing (RISC) microprocessor, very long instruction word (VLIW) microprocessor, or processor implementing other instruction sets, or processors implementing a combination of instruction sets. Processing device 602 may also be one or more special-purpose processing devices such as an application specific integrated circuit (ASIC), a field programmable gate array (FPGA), a digital signal processor (DSP), network processor, or the like. The processing device 602 is configured to execute instructions 626 for performing the operations and steps discussed herein.

The computer system 600 may further include a network interface device 608 to communicate over the network 620. The computer system 600 also may include a video display unit 610 (e.g., a liquid crystal display (LCD) or a cathode ray tube (CRT)), an alphanumeric input device 612 (e.g., a keyboard), a cursor control device 614 (e.g., a mouse), a graphics processing unit 622, a signal generation device 616 (e.g., a speaker), graphics processing unit 622, video processing unit 628, and audio processing unit 632.

The data storage device 618 may include a machine-readable storage medium 624 (also known as a computer-readable medium) on which is stored one or more sets of instructions or software 626 embodying any one or more of the methodologies or functions described herein. The instructions 626 may also reside, completely or at least partially, within the main memory 604 and/or within the processing device 602 during execution thereof by the computer system 600, the main memory 604 and the processing device 602 also constituting machine-readable storage media.

In one implementation, the instructions 626 include instructions to implement functionality corresponding to the components of a device to perform the disclosure herein. While the machine-readable storage medium 624 is shown in an example implementation to be a single medium, the term "machine-readable storage medium" should be taken to include a single medium or multiple media (e.g., a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present disclosure. The term "machine-readable storage medium" shall accordingly be taken to include, but not be limited to, solid-state memories, optical media and magnetic media.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "identifying" or "determining" or "executing" or "performing" or "collecting" or "creating" or "sending" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage devices.

The present disclosure also relates to an apparatus for performing the operations herein. This apparatus may be specially constructed for the intended purposes, or it may comprise a general purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

Various general purpose systems may be used with programs in accordance with the teachings herein, or it may prove convenient to construct a more specialized apparatus to perform the method. The structure for a variety of these systems will appear as set forth in the description above. In addition, the present disclosure is not described with reference to any particular programming language. It will be appreciated that a variety of programming languages may be used to implement the teachings of the disclosure as described herein.

The present disclosure may be provided as a computer program product, or software, that may include a machine-readable medium having stored thereon instructions, which may be used to program a computer system (or other electronic devices) to perform a process according to the present disclosure. A machine-readable medium includes any mechanism for storing information in a form readable by a machine (e.g., a computer). For example, a machine-readable (e.g., computer-readable) medium includes a machine (e.g., a computer) readable storage medium such as a read only memory ("ROM"), random access memory ("RAM"), magnetic disk storage media, optical storage media, flash memory devices, etc.

In the foregoing disclosure, implementations of the disclosure have been described with reference to specific example implementations thereof. It will be evident that various modifications may be made thereto without departing from the broader spirit and scope of implementations of the disclosure as set forth in the following claims. The disclosure and drawings are, accordingly, to be regarded in an illustrative sense rather than a restrictive sense.

What is claimed is:

1. A computer-implemented method comprising:

defining a display position of an image plane proximate to a current position of an ultrasound probe instrument, the ultrasound probe instrument visible in an Augmented Reality (AR) environment generated by an AR headset device;

rendering an AR situated view on the image plane in the AR environment, the situated view portraying ultrasound imagery captured by the ultrasound probe instrument, the ultrasound probe capturing ultrasound data captured in a three-dimensional coordinate system shared with the AR headset device;

continuously tracking a current position and orientation of the ultrasound probe, relative to continuous changes in position and orientation of the headset within the shared coordinate system;

generating a headset viewer, comprising the AR environment;

when the headset moves from a first position to a second position, re-rendering the AR environment, based on the position and orientation of the AR headset;

identifying image content of the situated view when the headset was in the first position and orientation;

adjusting a plane of the situated view, such that the plane is viewable in the headset viewer based on changes to the position of the AR headset, while the ultrasound imagery portrayed within the situated view is updated only based on a current position and orientation of the ultrasound probe and not the AR headset;

determining an AR display orientation of the image plane based on one or more detected movements of the AR headset device; and registering one or more portions of the ultrasound imagery as being representative of respective portions of a three-dimensional (3D) medical model.

2. The computer-implemented method of claim 1, wherein registering one or more portions of the ultrasound imagery comprises:

receiving one or more adjustments to a position and an orientation of a rendering of the 3D medical model displayed in the AR environment, the 3D medical model representing physical anatomy portrayed by the ultrasound imagery of the situated view; and receiving a selection indicating alignment of the 3D medical model and the ultrasound imagery of the situated view.

3. The computer-implemented method of claim 1, further comprising:

receiving a calibration selection that corresponds to ultrasound imagery depth.

4. The computer-implemented method of claim 3, further comprising:

receiving an assignment of a measure of distance per pixel of the situated view.

5. The computer-implemented method of claim 1, wherein determining the AR display orientation of the image plane comprises:

determining a first display orientation of the image plane based on a current position and orientation of an AR headset device;

detecting one or more changes to the current position and orientation of an AR headset device; and determining a second display orientation of the image plane based on the one or more changes to the position and orientation of an AR headset device.

6. The computer-implemented method of claim 5, wherein rendering the situated view at the image plane comprises:

rendering first ultrasound image content portrayed by the situated view at the first display position of the image plane according to the first image plane display orientation, the first display position of the image plane and the first ultrasound image content corresponding to a first position of the ultrasound probe instrument.

7. The computer-implemented method of claim 6, wherein rendering the situated view comprises:

rendering second ultrasound image content portrayed by the situated view at the second display position of the image plane according to the first ultrasound image content in the first image plane display orientation, the second display position of the image plane and the second ultrasound image content corresponding to a subsequent second position of the ultrasound probe instrument.

8. The computer-implemented method of claim 7, further comprising:

rendering the first ultrasound image content portrayed by the situated view at the first display position of the image plane according to the second image plane display orientation, the first display position of the image plane and the first ultrasound image content corresponding to a first position of the ultrasound probe instrument, the second image plane display orientation corresponding to one or more changes to the current position and orientation of an AR headset device.

9. A system comprising one or more processors, and a non-transitory computer-readable medium including one or more sequences of instructions that, when executed by the one or more processors, cause the system to perform operations comprising:

defining a display position of an image plane proximate to a current position of an ultrasound probe instrument, the ultrasound probe instrument visible in an Augmented Reality (AR) environment generated by an AR headset device;

rendering an AR situated view on the image plane in the AR environment, the situated view portraying ultrasound imagery captured by the ultrasound probe instrument, the ultrasound probe capturing ultrasound data captured in a three-dimensional coordinate system shared with the AR headset device;

continuously tracking a current position and orientation of the ultrasound probe, relative to continuous changes in position and orientation of the headset within the shared coordinate system;

generating a headset viewer, comprising the AR environment;

when the headset moves from a first position to a second position, re-rendering the AR environment, based on the position and orientation of the AR headset;

identifying image content of the situated view when the headset was in the first position and orientation;

adjusting a plane of the situated view, such that the plane is viewable in the headset viewer based on changes to the position of the AR headset, while the ultrasound imagery portrayed within the situated view is updated only based on a current position and orientation of the ultrasound probe and not the AR headset;

determining an AR display orientation of the image plane based on one or more detected movements of the AR headset device; and registering one or more portions of the ultrasound imagery as being representative of respective portions of a three-dimensional (3D) medical model.

10. The system of claim 9, wherein registering one or more portions of the ultrasound imagery comprises:

receiving one or more adjustments to a position and an orientation of a rendering of the 3D medical model displayed in the AR environment, the 3D medical model representing physical anatomy portrayed by the ultrasound imagery of the situated view; and receiving a selection indicating alignment of the 3D medical model and the ultrasound imagery of the situated view.

11. The system of claim 9, further comprising:

receiving a calibration selection that corresponds to ultrasound imagery depth.

12. The system of claim 11, further comprising:

receiving an assignment of a measure of distance per pixel of the situated view.

13. The system of claim 9, wherein determining the AR display orientation of the image plane comprises:

determining a first display orientation of the image plane based on a current position and orientation of an AR headset device;

detecting one or more changes to the current position and orientation of an AR headset device; and determining a second display orientation of the image plane based on the one or more changes to the position and orientation of an AR headset device.

14. The system of claim 13, wherein rendering the situated view at the image plane comprises:

rendering first ultrasound image content portrayed by the situated view at the first display position of the image plane according to the first image plane display orientation, the first display position of the image plane and the first ultrasound image content corresponding to a first position of the ultrasound probe instrument.

15. The system of claim 14, wherein rendering the situated view comprises:

rendering second ultrasound image content portrayed by the situated view at the second display position of the image plane according to the first ultrasound image content the first image plane display orientation, the second display position of the image plane and the second ultrasound image content corresponding to a subsequent second position of the ultrasound probe instrument.

16. The system of claim 15, further comprising:

rendering the first ultrasound image content portrayed by the situated view at the first display position of the image plane according to the second image plane display orientation, the first display position of the image plane and the first ultrasound image content corresponding to a first position of the ultrasound probe instrument, the second image plane display orientation corresponding to one or more changes to the current position and orientation of an AR headset device.

17. A computer program product comprising a non-transitory computer-readable medium having a computer-readable program code embodied therein to be executed by one or more processors, the program code including instructions to perform:

defining a display position of an image plane proximate to a current position of an ultrasound probe instrument, the ultrasound probe instrument visible in an Augmented Reality (AR) environment generated by an AR headset device;

rendering an AR situated view on the image plane in the AR environment, the situated view portraying ultrasound imagery captured by the ultrasound probe instrument, the ultrasound probe capturing ultrasound data captured in a three-dimensional coordinate system shared with the AR headset device;

continuously tracking a current position and orientation of the ultrasound probe, relative to continuous changes in position and orientation of the headset within the shared coordinate system;

generating a headset viewer, comprising the AR environment;

when the headset moves from a first position to a second position, re-rendering the AR environment, based on the position and orientation of the AR headset;

identifying image content of the situated view when the headset was in the first position and orientation;

adjusting a plane of the situated view, such that the plane is viewable in the headset viewer based on changes to the position of the AR headset, while the ultrasound imagery portrayed within the situated view is updated only based on a current position and orientation of the ultrasound probe and not the AR headset;

determining an AR display orientation of the image plane based on one or more detected movements of the AR headset device; and registering one or more portions of the ultrasound imagery as being representative of respective portions of a three-dimensional (3D) medical model.

18. The computer program product of claim 17, wherein registering one or more portions of the ultrasound imagery comprises:

receiving one or more adjustments to a position and an orientation of a rendering of the 3D medical model displayed in the AR environment, the 3D medical model representing physical anatomy portrayed by the ultrasound imagery of the situated view; and receiving a selection indicating alignment of the 3D medical model and the ultrasound imagery of the situated view.

19. The computer program product of claim 17, wherein determining the AR display orientation of the image plane comprises:

determining a first display orientation of the image plane based on a current position and orientation of an AR headset device;

detecting one or more changes to the current position and orientation of an AR headset device; and determining a second display orientation of the image plane based on the one or more changes to the position and orientation of an AR headset device.

20. The computer program product of claim 19, further comprising:

rendering first ultrasound image content portrayed by the situated view at the first display position of the image plane according to the first image plane display orientation, the first display position of the image plane and the first ultrasound image content corresponding to a first position of the ultrasound probe instrument; and rendering second ultrasound image content portrayed by the situated view at the second display position of the image plane according to the first ultrasound image content in the first image plane display orientation, the second display position of the image plane and the second ultrasound image content corresponding to a subsequent second position of the ultrasound probe instrument.

* * * * *